(12) United States Patent
Bass

(10) Patent No.: US 6,420,180 B1
(45) Date of Patent: Jul. 16, 2002

(54) MULTIPLE PASS DEPOSITION FOR CHEMICAL ARRAY FABRICATION

(75) Inventor: Jay K. Bass, Mountain View, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/491,692

(22) Filed: Jan. 26, 2000

(51) Int. Cl.$^7$ .................................................. G01N 1/10
(52) U.S. Cl. ........................... 436/43; 422/63; 422/100; 435/6; 435/287.2; 435/287.3; 436/43; 436/180; 436/518; 436/808; 536/25.3
(58) Field of Search ....................... 435/6, 287.3, 287.2; 436/164, 165, 514, 519, 807, 808, 43, 180, 518, 174; 422/50, 62, 82.05, 99, 100, 101, 102, 129, 131, 132, 134, 63; 536/25.3, 22.1, 24.3, 24.31; 346/140.1

(56) References Cited

U.S. PATENT DOCUMENTS

| | | | | |
|---|---|---|---|---|
| 5,847,105 A | * | 12/1998 | Baldeschwieier et al. ...... | 435/6 |
| 5,925,732 A | * | 7/1999 | Ecker et al. .................... | 435/6 |
| 5,981,733 A | * | 11/1999 | Gamble et al. ................ | 435/6 |
| 6,100,026 A | * | 8/2000 | Nova et al. .................... | 435/6 |
| 6,117,558 A1 | * | 1/2001 | Brennan et al. ........... | 536/25.3 |
| 6,228,659 B1 | * | 5/2001 | Kowallis et al. ............ | 436/180 |
| 6,242,266 B1 | * | 6/2001 | Schleifer et al. ............ | 436/518 |
| 6,306,599 B1 | * | 10/2001 | Perbost ........................... | 435/6 |
| 6,323,043 B1 | * | 11/2001 | Caren et al. ................ | 436/518 |

* cited by examiner

*Primary Examiner*—Joseph W. Drodge
(74) *Attorney, Agent, or Firm*—Gordon M. Stewart

(57) ABSTRACT

A method, apparatus, and computer program products, for forming an addressable array on a substrate. In the method, for each of multiple addresses on the substrate, a reagent drop set is deposited during a cycle so as to attach a corresponding moiety for that address. The foregoing step is repeated as required, until the addressable array is formed. The reagent drop set deposited during one or more cycles for one or more of the multiple addresses includes, for a corresponding cycle and address, drops of a same reagent which are deposited from different deposition units during the same cycle.

32 Claims, 4 Drawing Sheets

MULTIPLE PASS DEPOSITION FOR CHEMICAL ARRAY FABRICATION

FIELD OF THE INVENTION

This invention relates to arrays, particularly polynucleotide arrays such as DNA arrays, which are useful in diagnostic, screening, gene expression analysis, and other applications.

BACKGROUND OF THE INVENTION

Polynucleotide arrays (such as DNA or RNA arrays), are known and are used, for example, as diagnostic or screening tools. Such arrays include regions of usually different sequence polynucleotides arranged in a predetermined configuration on a substrate. These regions (sometimes referenced as "features") are positioned at respective locations ("addresses") on the substrate. The arrays, when exposed to a sample, will exhibit an observed binding pattern. This binding pattern can be detected upon interrogating the array. For example all polynucleotide targets (for example, DNA) in the sample can be labeled with a suitable label (such as a fluorescent compound), and the fluorescence pattern on the array accurately observed following exposure to the sample. Assuming that the different sequence polynucleotides were correctly deposited in accordance with the predetermined configuration, then the observed binding pattern will be indicative of the presence and/or concentration of one or more polynucleotide components of the sample.

Biopolymer arrays can be fabricated by depositing previously obtained biopolymers (such as from synthesis or natural sources) onto a substrate, or by in situ synthesis methods. Methods of depositing obtained biopolymers include loading then touching a pin or capillary to a surface, such as described in U.S. Pat. No. 5,807,522 or deposition by firing from a pulse jet such as an inkjet head, such as described in PCT publications WO 95/25116 and WO 98/41531, and elsewhere. Such a deposition method can be regarded as forming each feature by one cycle of attachment (that is, there is only one cycle at each feature during which the previously obtained biopolymer is attached to the substrate). For in situ fabrication methods, multiple different reagent droplets are deposited by pulse jet or other means at a given target location in order to form the final feature (hence a probe of the feature is synthesized on the array substrate). The in situ fabrication methods include those described in U.S. Pat. No. 5,449,754 for synthesizing peptide arrays, and described in WO 98/41531 and the references cited therein for polynucleotides, and may also use pulse jets for depositing reagents. The in situ method for fabricating a polynucleotide array typically follows, at each of the multiple different addresses at which features are to be formed, the same conventional iterative sequence used in forming polynucleotides from nucleoside reagents on a support by means of known chemistry. This iterative sequence can be considered as multiple ones of the following attachment cycle at each feature to be formed: (a) coupling a selected nucleoside (a monomeric unit) through a phosphite linkage to a functionalized support in the first iteration, or a nucleoside bound to the substrate (i.e. the nucleoside-modified substrate) in subsequent iterations; (b) optionally, but preferably, blocking unreacted hydroxyl groups on the substrate bound nucleoside; (c) oxidizing the phosphite linkage of step (a) to form a phosphate linkage; and (d) removing the protecting group ("deprotection") from the now substrate bound nucleoside coupled in step (a), to generate a reactive site for the next cycle of these steps. The functionalized support (in the first cycle) or deprotected coupled nucleoside (in subsequent cycles) provides a substrate bound moiety with a linking group for forming the phosphite linkage with a next nucleoside to be coupled in step (a). Final deprotection of nucleoside bases can be accomplished using alkaline conditions such as ammonium hydroxide, in a known manner. Conventionally, a single pulse jet or other deposition unit is assigned to deposit a single monomeric unit.

The foregoing chemistry of the synthesis of polynucleotides is described in detail, for example, in Caruthers, Science 230: 281–285, 1985; Itakura et al., *Ann. Rev. Biochem.* 53: 323–356; Hunkapillar et al., *Nature* 310: 105–110, 1984; and in "Synthesis of Oligonucleotide Derivatives in Design and Targeted Reaction of Oligonucleotide Derivatives", CRC Press, Boca Raton, Fla., pages 100 et seq., U.S. Pat. No. 4,458,066, U.S. Pat. No. 4,500,707, U.S. Pat. No. 5,153,319, U.S. Pat. No. 5,869,643, EP 0294196, and elsewhere. The phosphoramidite and phosphite triester approaches are most broadly used, but other approaches include the phosphodiester approach, the phosphotriester approach and the H-phosphonate approach. The substrates are typically functionalized to bond to the first deposited monomer. Suitable techniques for functionalizing substrates with such linking moieties are described, for example, in Southern, E. M., Maskos, U. and Elder, J. K., Genomics, 13, 1007–1017, 1992.

In the case of array fabrication, different monomers may be deposited at different addresses on the substrate during any one cycle so that the different features of the completed array will have different desired biopolymer sequences. One or more intermediate further steps may be required in each cycle, such as the conventional oxidation and washing steps in the case of in situ fabrication of polynucleotide arrays.

In array fabrication, the quantities of polynucleotide available are usually very small and expensive. Additionally, sample quantities available for testing are usually also very small and it is therefore desirable to simultaneously test the same sample against a large number of different probes on an array. These conditions require use of arrays with large numbers of very small, closely spaced features. It is important in such arrays that features actually be present, that they are put down as accurately as possible in the desired target pattern, are of the correct size, and that the DNA is uniformly coated within the feature. If any of these conditions are not met within a reasonable tolerance, the results obtained from a given array may be unreliable and misleading. This of course can have serious consequences to diagnostic, screening, gene expression analysis or other purposes for which the array is being used.

However, in any system used to fabricate arrays with the required small features, there is inevitably some degree of error, either fixed (and hence repeated) and/or random. In the case of both the deposition of previously obtained biopolymers, but particularly in the in situ fabrication method, drop deposition errors from cycle to cycle may be different and are cumulative in determining errors in the finally formed features. For example, polynucleotide arrays formed by the in situ method will have actual features represented only by the region where droplets of nucleoside monomers have overlapped (that is, the intersection of the nucleoside monomer droplets deposited during multiple cycles). The present invention realizes that in the conventional in situ system where a single pulse jet deposits all of a particular nucleoside monomer unit during a cycle, a serious trajectory error in just one such pulse jet will result in a serious error in the resulting feature (that is, the feature will be seriously smaller than expected). Furthermore, if one such pulse jet fails to fire during a single cycle at a feature, the resulting feature will effectively be useless (since it will be capped in the capping step or, where no capping step is used, will be missing a nucleotide and therefore will have the wrong sequence). It has been known to use multiple firings of a same reagent from a same pulse jet, during a same cycle. While this reduces random errors which might occur during a pulse jet firing, it does not correct for a fixed trajectory error of a pulse jet, nor will it correct for failure of that pulse jet.

It would be desirable then to provide a means by which serious errors in features formed during an in situ or any array fabrication method, can be reduced. It would further be desirable if the results of fixed errors in a drop deposition unit (such as a pulse jet of a multiple pulse jet system) can be reduced.

SUMMARY OF THE INVENTION

The present invention further realizes that serious errors in features during array formation, resulting from a serious error (including failure) of a drop deposition unit in a multiple drop deposition unit system, can be reduced by using multiple different drop deposition units to deposit the same reagent in any given cycle. As a result, while a feature in such a case may not be ideal, the error which might otherwise occur can be substantially reduced.

The present invention then, provides a method of forming an addressable array on a substrate. For each of multiple addresses on the substrate, a reagent drop set is deposited during a cycle so as to attach a corresponding moiety for that address. The foregoing step can be repeated as required, until the addressable array is formed. The reagent drop set deposited during one or more cycles for one or more of the multiple addresses includes, for a corresponding cycle and address, drops of a same reagent (which drops may or may not be of the same total composition) which are deposited from different deposition units during the same cycle. Such a method can be used where the array has features of any chemical moieties. For example, where the features are polymers, such as polynucleotides or peptides, the drops of the same reagent may include a same polymer (where the array is being formed in one cycle for each address by deposition of the previously obtained polymer, such as a polynucleotide or peptide) or a same monomeric unit (where the array is being formed in multiple cycles for each address during the in situ method, such as a same nucleoside monomer or same amino acid monomer).

In one aspect of the method, at least some of the deposition units are in a first line. The deposition units or the substrate, or both, is moved along a line parallel to the first line so as to form an addressable array with features in a line parallel to the first line. The drops of a same reagent deposited from different deposition units during the same cycle for an address, are deposited from different deposition units along the first line. The first line may, for example, be a straight or curved line.

In a particular configuration, the deposition units may be part of a same head so as to move as one unit, with at least the head being moved with respect to the substrate.

The present invention also provides an apparatus for forming an addressable array on a substrate, which can execute one or more methods of the present invention. In one aspect, the apparatus includes a deposition system having multiple deposition units (for example, pulse jets) each of which can dispense a reagent drop. A transport system moves at least one of the deposition system or the substrate. A processor controls the deposition system and the transport system. The processor control is such that for each of multiple addresses on the substrate, a reagent drop set is deposited by the deposition system during a cycle so as to attach a corresponding moiety for that address. Further, the processor control causes the foregoing step to be repeated if required, until the addressable array is formed. The processor control also ensures that the reagent drop set deposited during one or more cycles for one or more of the multiple addresses includes, for a corresponding cycle and address, drops of a same reagent which are deposited from different deposition units during the same cycle.

In the apparatus at least some of the deposition units may be in a first line and the apparatus includes a transport system to move at least one of the deposition system or substrate, both as described above. In this case, the processor may cause the drops of the same reagent to be deposited from different deposition units along the first line, during the same cycle for an address.

A further aspect of the present invention provides a method of determining a reagent drop deposition pattern for forming an addressable array. In this method, a target layout (sometimes referenced as an "aim layout") for an addressable array is obtained. The reagent drop deposition pattern is determined from the target layout and the number of drop deposition units in a drop deposition system which includes multiple deposition units. By "determined" in the foregoing aspect is referenced that the drop deposition pattern is obtained using the described items, but additional elements can also be taken into account. The determined drop deposition pattern includes a definition of, for each of multiple addresses on the substrate, a reagent drop set which is to be deposited during a cycle so as to attach a corresponding moiety for that address. The determined pattern further includes repetitions of the foregoing step as required, until the addressable array is formed. In the determined pattern, the reagent drop set deposited during one or more cycles for one or more of the multiple addresses includes, for a corresponding cycle and address, drops of a same reagent which are deposited from different deposition units during the same cycle.

The present invention further provides a computer program product which can execute any one or more methods of the present invention. Optionally, the present invention may further provide for exposing the array to a sample, and interrogating the array following the exposure and optionally processing results of the interrogation. Such an interrogation or processing result may be forwarded to a remote location. The present invention also provides a method in which data is transmitted representing a drop deposition pattern produced in one or more of the methods of the present invention.

The various aspects of the present invention can provide any one or more of the following and/or other useful benefits. For example, serious errors in features formed during an in situ or any array fabrication method, can be reduced. Further, the results of fixed errors in a drop deposition unit (such as a pulse jet of a multiple pulse jet system) can be reduced.

BRIEF DESCRIPTION OF THE DRAWINGS

To facilitate understanding, identical reference numerals have been used, where practical, to designate identical elements that are common to the figures.

DETAILED DESCRIPTION OF EMBODIMENTS OF THE INVENTION

Figure 1:
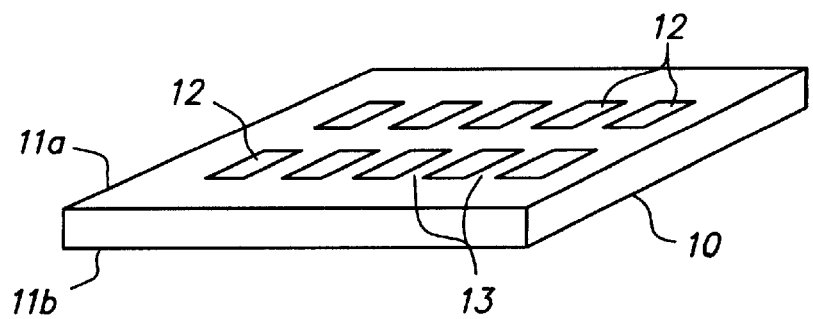
FIG. 1 illustrates a substrate carrying multiple arrays, such as may be fabricated by methods of the present invention.

In the present application, unless a contrary intention appears, the following terms refer to the indicated characteristics. A "biopolymer" is a polymer of one or more types of repeating units. Biopolymers are typically found in biological systems and particularly include peptides or polynucleotides, as well as such compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. For example, a "biopolymer" includes DNA (including cDNA), RNA, oligonucleotides, and PNA and other polynucleotides as described in U.S. Pat. No. 5,948,902 and references cited therein (all of which are incorporated herein by reference), regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution).

A "set" of drops generally, may contain only one, or only two, or three, or any number of multiple drops (although where "drops" are referenced in relation to a set implies the set in that case includes multiple drops). An "array", unless a contrary intention appears, includes any one, two or three dimensional arrangement of addressable regions bearing a particular chemical moiety or moieties (for example, biopolymers such as polynucleotide sequences) associated with that region. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other). An "array layout" refers collectively to one or more characteristics of the features, such as feature positioning, one or more feature dimensions, and some indication of a moiety at a given location. "Hybridizing" and "binding", with respect to polynucleotides, are used interchangeably. During a "cycle" for forming a given feature, typically at least 50% (and more typically at least 70%, 80% or more preferably at least 90% or 95%) of moieties bound to a substrate surface available to link with a deposited monomeric unit or previously obtained complete moiety for forming the desired feature, actually link to such deposited monomeric unit or complete moiety.

When one item is indicated as being "remote" from another, this is referenced that the two items are at least in different buildings, and may be at least one mile, ten miles, or at least one hundred miles apart. "Communicating" information references transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top", "upper", and "lower" are used in a relative sense only. "Fluid" is used herein to reference a liquid. Reference to a singular item, includes the possibility that there are plural of the same items present. All patents and other cited references are incorporated into this application by reference.

Figure 2:
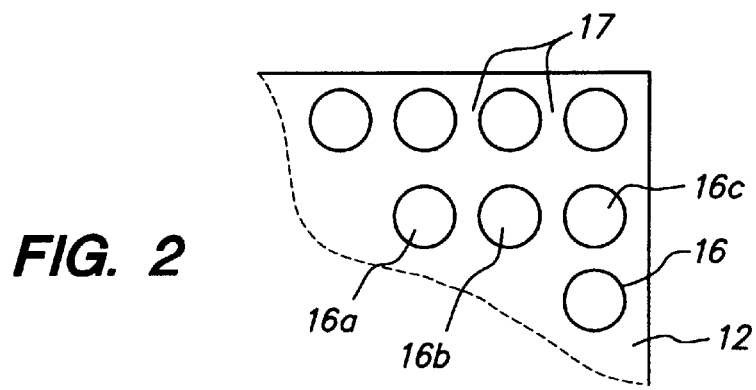
FIG. 2 is an enlarged view of a portion of FIG. 1 showing multiple ideal spots or features.
Figure 3:
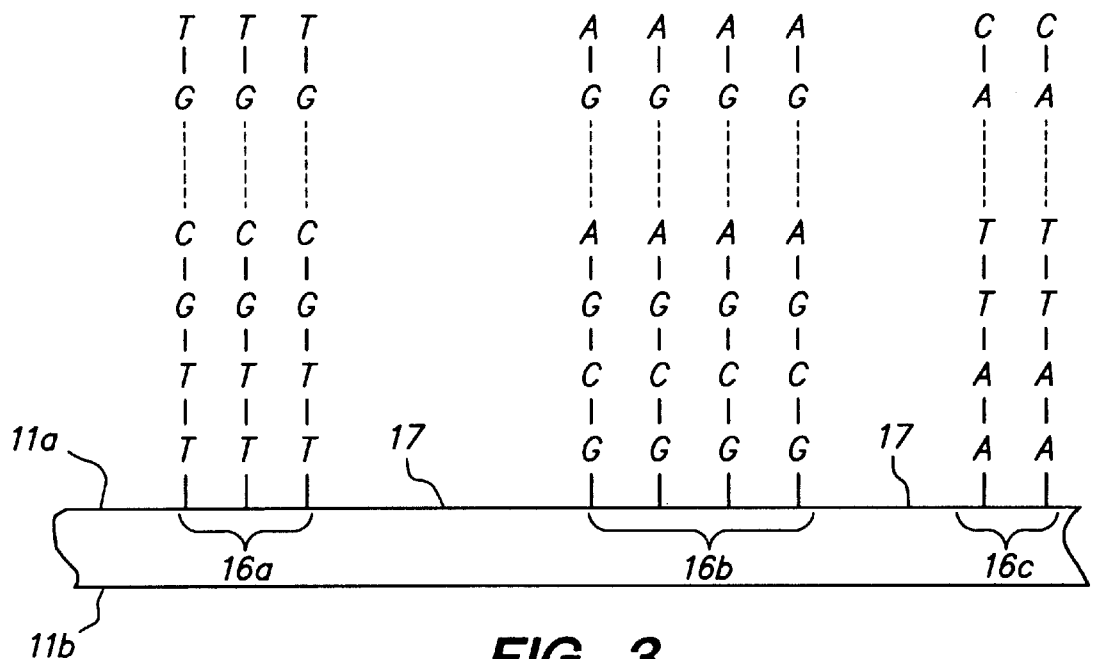
FIG. 3 is an enlarged illustration of a portion of the substrate in FIG. 2.

Referring first to FIGS. 1–3, typically methods and apparatus of the present invention generate or use a contiguous planar substrate 10 carrying one or more arrays 12 disposed across a front surface 11a of substrate 10 and separated by inter-array areas 13. A back side 11b of substrate 10 does not carry any arrays 12. The arrays on substrate 10 can be designed for testing against any type of sample, whether a trial sample, reference sample, a combination of them, or a known mixture of polynucleotides (in which latter case the arrays may be composed of features carrying unknown sequences to be evaluated). While ten arrays 12 are shown in FIG. 1 and the different embodiments described below may use substrates with particular numbers of arrays, it will be understood that substrate 10 and the embodiments to be used with it, may use any number of desired arrays 12. Similarly, substrate 10 may be of any shape, and any apparatus used with it adapted accordingly. Depending upon intended use, any or all of arrays 12 may be the same or different from one another and each will contain multiple spots or features 16 of biopolymers in the form of polynucleotides. A typical array may contain from more than ten, more than one hundred, more than one thousand or ten thousand features, or even more than from one hundred thousand features. All of the features 16 may be different, or some or all could be the same. In the case where arrays 12 are formed by the conventional in situ or deposition of previously obtained moieties, as described above, by depositing for each feature a droplet of reagent in each cycle such as by using a pulse jet such as an inkjet type head, interfeature areas 17 will typically be present which do not carry any polynucleotide. It will be appreciated though, that the interfeature areas 17 could be of various sizes and configurations. It will also be appreciated that there need not be any space separating arrays 12 from one another. Each feature carries a predetermined polynucleotide (which includes the possibility of mixtures of polynucleotides). As per usual, A, C, G, T represent the usual nucleotides. It will be understood that there is usually a linker molecule (not shown) of any known types between the front surface 11a and the first nucleotide.

FIGS. 2 and 3 illustrate ideal features where. the actual features formed are the same as the target (or "aim") features, with each feature 16 being uniform in shape, size and composition, and the features being regularly spaced. Such an array when fabricated by drop deposition methods, would require all reagent droplets for each feature to be uniform in shape and accurately deposited at the target feature location. In practice, such an ideal result is difficult to obtain due to both the fixed and random errors such as those discussed above.

For the purposes of the discussions below, it will be assumed (unless the contrary is indicated) that the array being formed in any case is a polynucleotide array formed by the in situ method using pulse jet deposition units. However, the applicability of the method to arrays of other polymers or chemical moieties generally, whether formed by multiple cycle in situ methods or deposition of previously obtained moieties, or using other types of deposition units, will be understood from these discussions.

Figure 4:
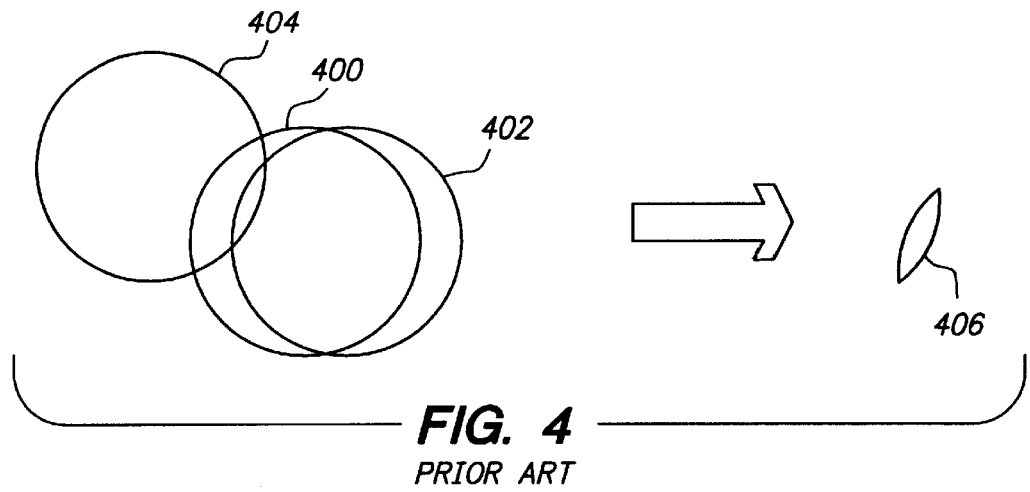
FIG. 4 illustrates the result of reagent drop placement error during two cycles of a conventional array feature formation method.
Figure 5:
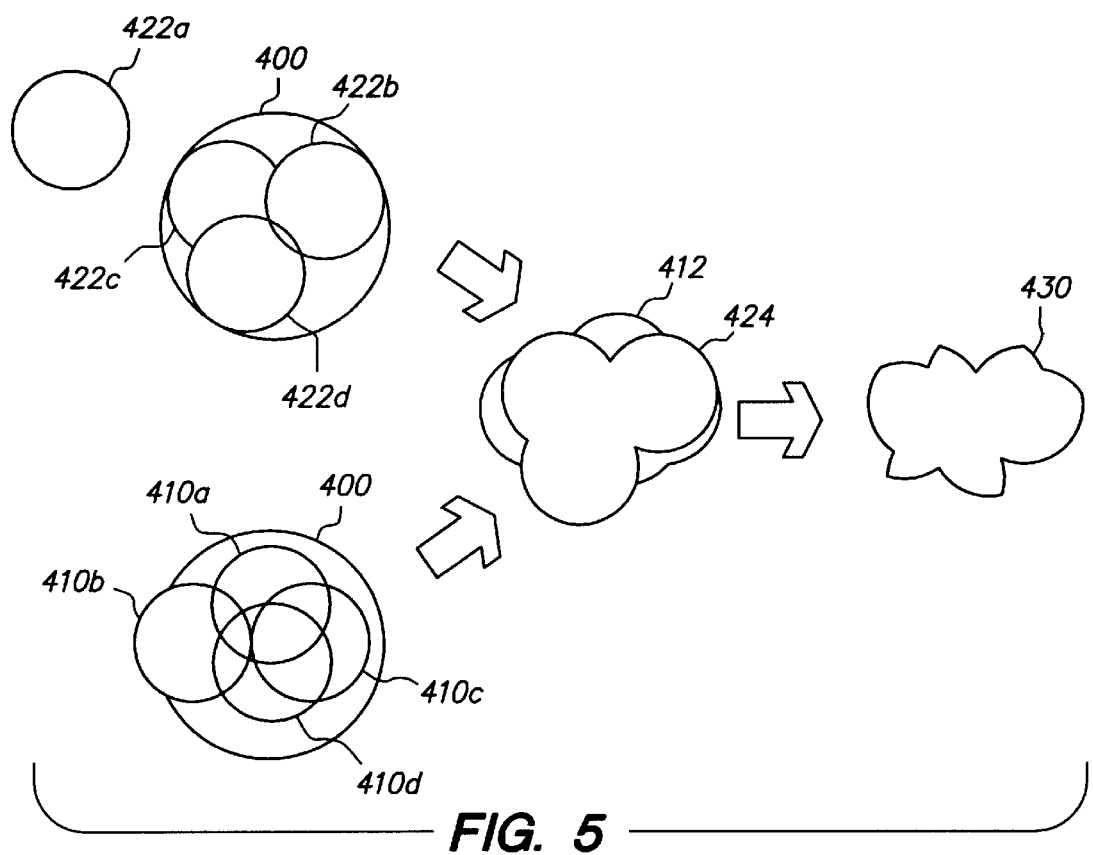
FIG. 5 illustrates the result of a similar reagent drop placement error during two cycles, using a method of the present invention.

FIGS. 4 and 5 illustrate how the method of the present invention can reduce serious errors in array formation. FIG. 4 illustrates the result of reagent drop placement error during two cycles of a conventional in situ array feature formation method, at a single feature. The region on a substrate to be covered by an ideal target feature 400, is defined by the layout of the array to be fabricated. Ideally, all nucleoside phosphoramidite (sometimes referenced herein simply as "phosphoramidite") drops deposited should cover the region defined by target feature 400. In practice, in one cycle a pulse jet arbitrarily designated as pulse jet P1, deposits a reagent drop set in the form of a single drop containing a phosphoramidite reagent for a T which, due to a slight deviation in trajectory of pulse jet P1 from ideal, covers the region on the substrate referenced as spot 400 in FIG. 4 and attaches at that spot (either to the substrate, a linker on the substrate, or to a monomer deposited in a previous cycle). Similarly, in another cycle a pulse jet different from P1 and arbitrarily designated as pulse jet P5, deposits a reagent drop set in the form of a single drop 404 containing a phosphoramidite for a G which, due to a serious deviation in trajectory of pulse jet P5, covers the region referenced as spot 404. The best feature with the correct nucleotide sequence T-G that can be obtained as a result of the foregoing, is defined by the intersection of spots 402 and 404 and is shown as actual feature 406 in FIG. 4. Note that even if further cycles were to be executed to obtain a longer polynucleotide (such as a T-G-A-C and the like), the feature with the target sequence can, at best, only cover the region of actual feature 406. Such a feature exhibits a serious error versus the target feature 400, being both misplaced from the center of target feature 400 and being seriously deficient in size.

Turning now to FIG. 5, the same process as described in connection with FIG. 4 is repeated. However, in this case the reagent drop set for T contains into four drops of the same composition, which are deposited by respective different pulse jets P1 through P4 during a same cycle (the particular "T cycle") for target feature 400. Similarly, the reagent drop set for G contains four drops of the same composition, which are deposited by respective different pulse jets P5 through P8 during a same cycle (the particular "G cycle") for the target feature 400. In the case of the phosphoramidite reagent for T, even assuming that pulse jet P1 has the same serious trajectory error as discussed above in connection with FIG. 4, provided pulse jets P2 through P4 have more typical minor trajectory errors the resulting deposited drops will cover regions designated as spots 422a through 422d in FIG. 5 in relation to target feature 400. Since this is the same cycle, the region covered by the drop set for T is the union of spots 422b, 422c and 422d and is designated as T region 424 in FIG. 5 (422a will be ignored in G region 424 since its location is so seriously in error that it will not form target sequence with the G drops about to be described).

Similarly, in FIG. 5 during the other cycle the reagent drop set for G contains four drops of the same composition, which are deposited by respective different pulse jets P5 through P8 to form spots 410a to 410d (assuming only minor trajectory errors in each of the pulse jets) during a same cycle. The union of the region covered by the drop set for G then is designated G region 412 in FIG. 5.

The resulting actual feature 430 of sequence T-G formed by the process of FIG. and 5 will be the intersection of T region 424 and G region 412, as illustrated in FIG. 5. Note that even though in both the conventional method of FIG. 4 and the method of the present invention in FIG. 5, a pulse jet P1 has a serious trajectory error, the actual feature 430 resulting from the method of the present invention covers more area and is more closely aligned with the target feature 400 than the actual feature 406 resulting from the conventional method. Furthermore, in the situation where pulse jet P1 failed to fire in the conventional method of FIG. 4, no feature is produced. However, in the method of FIG. 4 even if pulse jet P1 (or any one of the pulse jets P1 through P4) fails to fire, a relatively good and useful feature (though not quite ideal) is still formed. Also, the method of depositing multiple same droplets from the same pulse jet, mentioned above, would not alter the result in FIG. 4 for a fixed trajectory error or firing problem of pulse jet P1. Thus, the method illustrated in FIG. 5 works whether the error in a given deposition unit is random or fixed.

Figure 6:
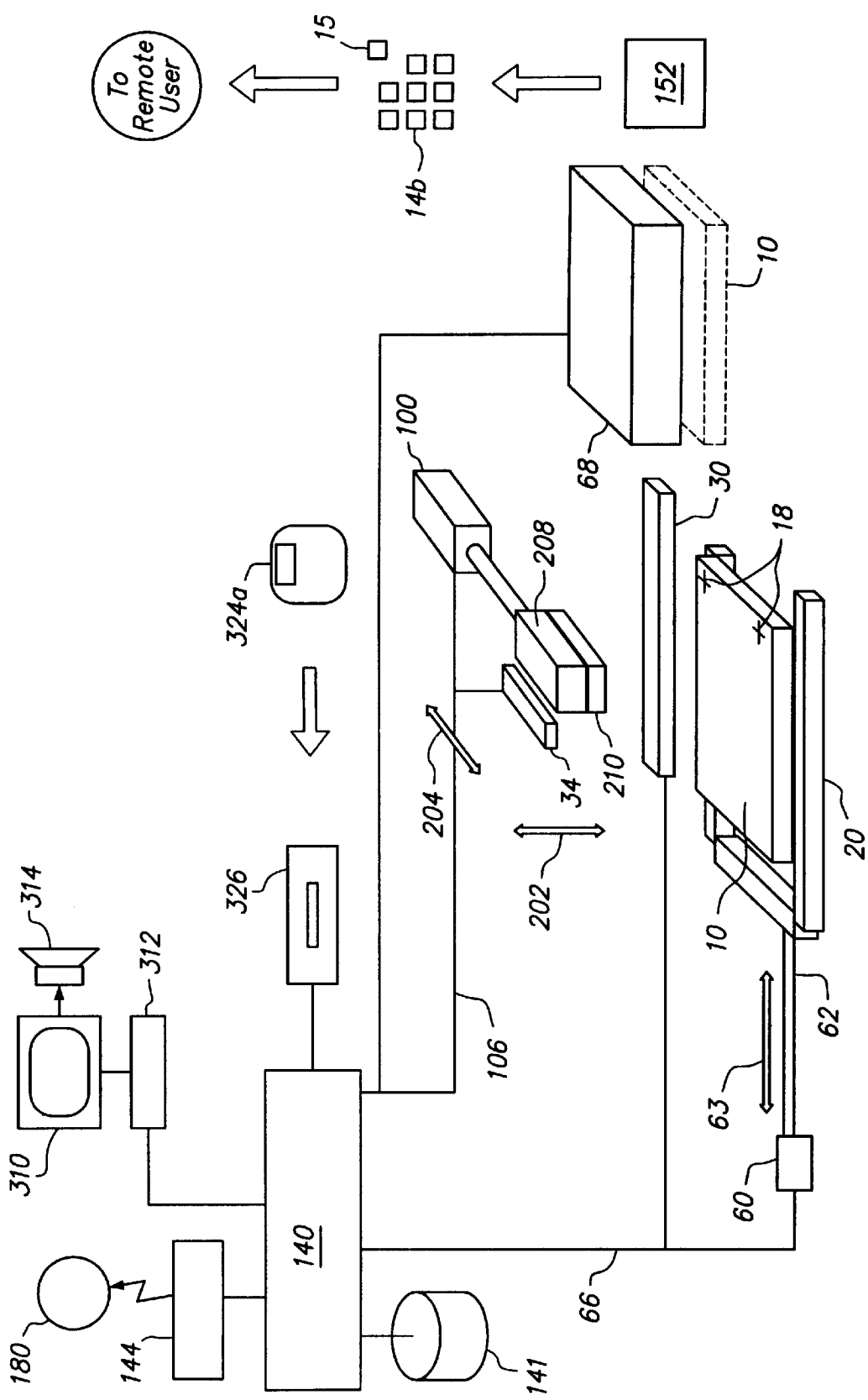
FIG. 6 is a schematic diagram illustrating a fabrication apparatus of the present invention.

Referring now to FIG. 6, an apparatus of the present invention which can execute a method of the present invention, will now be described. The apparatus shown includes a substrate station 20 on which can be mounted a substrate 10. Pins or similar means (not shown) can be provided on substrate station 20 by which to approximately align substrate 10 to a nominal position thereon (with alignment marks 18 on substrate 10 being used for more refined alignment). Substrate station 20 can include a vacuum chuck connected to a suitable vacuum source (not shown) to retain a substrate 14 without exerting too much pressure thereon, since substrate 14 is often made of glass. A flood station 68 is provided which can expose the entire surface of substrate 10, when positioned beneath station 68 as illustrated in broken lines in FIG. 4, to a fluid typically used in the in situ process, and to which all features must be exposed during each cycle (for example, oxidizer, deprotection agent, and wash buffer). In the case of deposition of a previously obtained polynucleotide, flood station 68 may not be present.

A dispensing head 210 is retained by a head retainer 208. The positioning system includes a carriage 62 connected to a first transporter 60 controlled by processor 140 through line 66, and a second transporter 100 controlled by processor 140 through line 106. Transporter 60 and carriage 62 are used execute one axis positioning of station 20 (and hence mounted substrate 10) facing the dispensing head 210, by moving it in the direction of arrow 63, while transporter 100 is used to provide adjustment of the position of head retainer 208 (and hence head 210) in a direction of axis 204. In this manner, head 210 can be scanned line by line, by scanning along a line over substrate 10 in the direction of axis 204 using transporter 100, while line by line movement of substrate 10 in a direction of axis 63 is provided by transporter 60. Transporter 60 can also move substrate holder 20 to position substrate 10 beneath flood station 68 (as illustrated by the substrate 10 shown in broken lines in FIG. 4). Head 210 may also optionally be moved in a vertical direction 202, by another suitable transporter (not shown). It will be appreciated that other scanning configurations could be used. It will also be appreciated that both transporters 60 and 100, or either one of them, with suitable construction, could be used to perform the foregoing scanning of head 210 with respect to substrate 10. Thus, when the present application recites "positioning" one element (such as head 210) in relation to another element (such as one of the stations 20 or substrate 10) it will be understood that any required moving can be accomplished by moving either element or a combination of both of them. The head 210, the positioning system, and processor 140 together act as the deposition system of the apparatus. An encoder 30 communicates with processor 140 to provide data on the exact location of substrate station 20 (and hence substrate 10 if positioned correctly on substrate station 20), while encoder 34 provides data on the exact location of holder 208 (and hence head 210 if positioned correctly on holder 208). Any suitable encoder, such as an optical encoder, may be used which provides data on linear position.

Processor 140 also has access through a communication module 144 to a communication channel 180 to communicate with a remote station. Communication channel 180 may, for example, be a Wide Area Network ("WAN"), telephone network, satellite network, or any other suitable communication channel.

Head 210 may be of a type commonly used in an ink jet type of printer and may, for example, include five or more chambers (at least one for each of four nucleoside phosphoramidite monomers plus at least one for an activator solution) each communicating with a corresponding set of multiple drop dispensing orifices and multiple ejectors which are positioned in the chambers opposite respective orifices. Each ejector is in the form of an electrical resistor operating as a heating element under control of processor 140 (although piezoelectric elements could be used instead). Each orifice with its associated ejector and portion of the chamber, defines a corresponding pulse jet. It will be appreciated that head 210 could, for example, have more or less pulse jets as desired (for example, at least ten or at least one hundred pulse jets). Application of a single electric pulse to an ejector will cause a droplet to be dispensed from a corresponding orifice. Certain elements of the head 210 can be adapted from parts of a commercially available thermal inkjet print head device available from Hewlett-Packard Co. as part no. HP51645A. Alternatively, multiple heads could be used instead of a single head 210, each being similar in construction to head 210 and being provided with respective transporters under control of processor 140 for independent movement. In this alternate configuration, each head may dispense a corresponding biomonomer (for example, one of four nucleoside phosphoramidites) or an activator solution.

As is well known in the ink jet print art, the amount of fluid that is expelled in a single activation event of a pulse jet, can be controlled by changing one or more of a number of parameters, including the orifice diameter, the orifice length (thickness of the orifice member at the orifice), the size of the deposition chamber, and the size of the heating element, among others. The amount of fluid that is expelled during a single activation event is generally in the range about 0.1 to 1000 pL, usually about 0.5 to 500 pL and more usually about 1.0 to 250 pL. A typical velocity at which the fluid is expelled from the chamber is more than about 1 m/s, usually more than about 10 m/s, and may be as great as about 20 m/s or greater. As will be appreciated, if the orifice is in motion with respect to the receiving surface at the time an ejector is activated, the actual site of deposition of the material will not be the location that is at the moment of activation in a line-of-sight relation to the orifice, but will be a location that is predictable for the given distances and velocities.

The apparatus can deposit droplets to provide features which may have widths (that is, diameter, for a round spot) in the range from a minimum of about 10 $\mu$m to a maximum of about 1.0 cm. In embodiments where very small spot sizes or feature sizes are desired, material can be deposited according to the invention in small spots whose width is in the range about 1.0 $\mu$m to 1.0 mm, usually about 5.0 $\mu$m to 500 $\mu$m, and more usually about 10 $\mu$m to 200 $\mu$m.

The apparatus further includes a display 310, speaker 314, and operator input device 312. Operator input device 312 may, for example, be a keyboard, mouse, or the like. Processor 140 has access to a memory 141, and controls print head 210 (specifically, the activation of the ejectors therein), operation of the positioning system, operation of each jet in print head 210, and operation of display 310 and speaker 314. Memory 141 may be any suitable device in which processor 140 can store and retrieve data, such as magnetic, optical, or solid state storage devices (including magnetic or optical disks or tape or RAM, or any other suitable device, either fixed or portable). Processor 140 may include a general purpose digital microprocessor suitably programmed from a computer readable medium carrying necessary program code, to execute all of the steps required by the present invention, or any hardware or software combination which will perform those or equivalent steps. The programming can be provided remotely to processor 141 through communication channel 180, or previously saved in a computer program product such as memory 141 or some other portable or fixed computer readable storage medium using any of those devices mentioned below in connection with memory 141. For example, a magnetic or optical disk 324a may carry the programming, and can be read by disk writer/reader 326. A cutter 152 is provided to cut substrate 10 into individual array units 15 each carrying a corresponding array 12.

The operation of the fabrication station will now be described. It will be assumed that a substrate 10 on which arrays 12 are to be fabricated, is in position on station 20 and that processor 140 is programmed with the necessary layout information to fabricate target arrays 12. Using information such as the foregoing target layout and the number and location of drop deposition units in head 210, processor 140 can then determine a reagent drop deposition pattern. Alternatively, such a pattern could have been determined by another processor (such as a remote processor) and communicated to memory 141 through communication channel 180 or by forwarding a portable storage medium carrying such pattern data for reading by reader/writer 326. Processor 140 controls fabrication, in accordance with the deposition pattern, to generate the one or more arrays on substrate 10 by depositing for each target feature during each cycle, a reagent drop set. The reagent drop set deposited during one or more cycles for one or more of the multiple addresses includes, for a corresponding cycle and address, drops of a same reagent which are deposited from different pulse jets during the same cycle. Processor 140 also sends substrate 10 to flood station 68 for intervening or final steps as required, all in accordance with the conventional in situ polynucleotide array fabrication process described above. The substrate 10 is then sent to a cutter 152 wherein portions of substrate 10 carrying an individual array 12 are separated from the remainder of substrate 10, to provide multiple array units 15. One or more array units may then be forwarded to one or more remote users.

The above sequence can be repeated at the fabrication station as desired for multiple substrates 10 in turn. As mentioned above, the fabrication station may act as a central fabrication station for each of multiple remote user stations, in the same manner as described above. When a user receives an array unit 15, it will typically be exposed to a sample and the array interrogated following exposure. Interrogation is usually accomplished by a suitable scanner which can read the location and intensity of fluorescence at each feature of an array following exposure to a fluorescently labeled sample. For example, such a scanner may be similar to the GENEARRAY scanner available from Hewlett-Packard, Palo Alto, Calif. Results from interrogation can be processed such as by rejecting a reading for a feature which is below a predetermined threshold and/or forming conclusions based on the pattern read from the array (such as whether or not a particular target sequence may have been present in the sample). The results of the interrogation or processing can be communicated to a remote location if desired, for further use.

In a variation of the above, it is possible that each unit 15 may be contained with a suitable housing. Such a housing may include a closed chamber accessible through one or more ports normally closed by septa, which carries the substrate 10.

Figure 7:
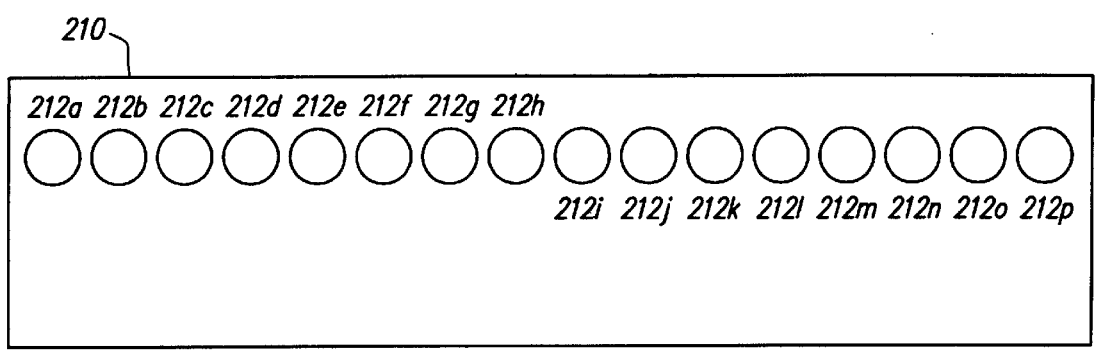
FIG. 7 is an enlarged view of a portion of the drop dispensing head of the apparatus of FIG. 6 and to illustrate a method of the present invention.

In one particular aspect of the present invention, the different deposition units from which the same droplets are deposited lie along a first line, and the substrate and/or the deposition units (for example, the head 210) is moved in a direction parallel to that line. Such a configuration is illustrated in FIG. 7. For simplicity it will be assumed that head 210 in this configuration has a single straight line of 16 jet nozzles 212a through 212p. However, it will be appreciated that other numbers of nozzles along the straight line and multiple lines, can be used in a similar manner as will now be described. In particular, in FIG. 7 head 210 has each set of four successive nozzles arranged to dispense the same phosphoramidite (A for nozzles 212a through 212d, T for 212e through 212h, G for 212i through 212l and C for 212m through 212p). For each of the addresses at which features 16b and 16c in FIG. 3 are to be formed by the in situ method, a reagent drop set is deposited so as to attach a corresponding phosphoramidite at that address during any one cycle. The reagent drop set deposited during each one of the cycles for each of features 16b, 16c includes, for a corresponding cycle and address, drops of a same reagent which are deposited from different deposition units during the same cycle. Thus, for a first cycle at feature 16b the reagent drop set consists of four drops of G phosphoramidite fired from respective different nozzles 212i through 212k. Head 210 or substrate 10 is moved along a line parallel to the first line along which nozzles 212a through 212p lie until each nozzle 212i through 212k is in turn directly over the target address for feature 16b. Similarly, for a first cycle at feature 16c the reagent drop set consist of four drops of A phosphoramidite fired from respective different nozzles 212a through 212d. During a second cycle for feature 16b the reagent drop set consists of four drops of C phosphoramidite fired from respective different nozzles 212m through 212p. During a second cycle for feature 16c the reagent drop set consist of four drops of A phosphoramidite fired from respective different nozzles 212a through 212d. This process is repeated at each of the target features as required until the target polynucleotides is formed at those features.

The foregoing configuration where the multiple deposition units for depositing a given droplet set are in a line parallel to the line of features to be formed, reduces the necessity of having to move the head more frequently back and forth across the line of features to be formed in order to deposit the drop set during a given cycle. It will be appreciated that where a similar advantage can be obtained where nozzles 212a through 212p lie along a curved first line where the features to be formed are also to lie along a curved line. In such an event one or both of head 210 and substrate 10 may be moved along a curved line parallel which will be parallel to such a curved first line. Also, the present method contemplates that in the case where a feature is desired to contain a mixture of polynucleotides, a droplet set may contain any required mixture of phosphoramidites for one or more cycles as required depending upon the polynucleotide mixture to be formed at that feature. It will also be appreciated that the four different nozzles dispensing the drops of the same phosphoramidite during a cycle, need not be successive on head 210. For example, the sixteen nozzles illustrated in FIG. 7 could be arranged along a straight line in the sequence (to dispense the various phosphoramidites) of A, T, G, C, A, T, G, C, A, T, G, C, A, T, G, C. Other configurations are of course also possible.

Modifications in the particular embodiments described above are, of course, possible. For example, where a pattern of arrays is desired, any of a variety of geometries may be constructed other than the organized rows and columns of arrays 12 of FIG. 1. For example, arrays 12 can be arranged in a series of curvilinear rows across the substrate surface (for example, a series of concentric circles or semi-circles of spots), and the like. Similarly, as mentioned, the pattern of features 16 may be varied from the organized rows and columns of spots in FIG. 2 to include, for example, a series of curvilinear rows across the substrate surface(for example, a series of concentric circles or semi-circles of spots), and the like.

The present methods and apparatus may be used to deposit biopolymers or other moieties on surfaces of any of a variety of different substrates, including both flexible and rigid substrates. Preferred materials provide physical support for the deposited material and endure the conditions of the deposition process and of any subsequent treatment or handling or processing that may be encountered in the use of the particular array. The array substrate may take any of a variety of configurations ranging from simple to complex. Thus, the substrate could have generally planar form, as for example a slide or plate configuration, such as a rectangular or square or disc. In many embodiments, the substrate will be shaped generally as a rectangular solid, having a length in the range about 4 mm to 200 mm, usually about 4 mm to 150 mm, more usually about 4 mm to 125 mm; a width in the range about 4 mm to 200 mm, usually about 4 mm to 120 mm and more usually about 4 mm to 80 mm; and a thickness in the range about 0.01 mm to 5.0 mm, usually from about 0.1 mm to 2 mm and more usually from about 0.2 to 1 mm. However, larger substrates can be used, particularly when such are cut after fabrication into smaller size substrates carrying a smaller total number of arrays 12. Substrates of other configurations and equivalent areas can be chosen. The configuration of the array may be selected according to manufacturing, handling, and use considerations.

The substrates may be fabricated from any of a variety of materials. In certain embodiments, such as for example where production of binding pair arrays for use in research and related applications is desired, the materials from which the substrate may be fabricated should ideally exhibit a low level of non-specific binding during hybridization events. In many situations, it may also be preferable to employ a material that is transparent to visible and/or UV light. For flexible substrates, materials of interest include: nylon, both modified and unmodified, nitrocellulose, polypropylene, and the like, where a nylon membrane, as well as derivatives thereof, may be particularly useful in this embodiment. For rigid substrates, specific materials of interest include: glass; fused silica, silicon, plastics (for example, polytetrafluoroethylene, polypropylene, polystyrene, polycarbonate, and blends thereof, and the like); metals (for example, gold, platinum, and the like).

The substrate surface onto which the polynucleotide compositions or other moieties is deposited may be porous or non-porous, smooth or substantially planar, or have irregularities, such as depressions or elevations. The surface may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof (for example, peptide nucleic acids and the like); polysaccharides, phospholipids, polyurethanes, polyesters, polycarbonates, polyureas, polyamides, polyethyleneamines, polyarylene sulfides, polysiloxanes, polyimides, polyacetates, and the like, where the polymers may be hetero- or homopolymeric, and may or may not have separate functional moieties attached thereto (for example, conjugated).

Various further modifications to the particular embodiments described above are, of course, possible. Accordingly, the present invention is not limited to the particular embodiments described in detail above.

What is claimed is:

1. A method of forming an addressable array on a substrate, comprising:
   (a) for each of multiple addresses on the substrate, depositing a reagent drop set during a cycle so as to attach a corresponding moiety for that address; and
   (b) repeating step (a) if required, until the addressable array is formed,
       wherein the reagent drop set deposited during one or more cycles for one or more of the multiple addresses includes, for a corresponding cycle and address, drops of a same reagent which are deposited from different deposition units during the same cycle.

2. A method according to claim 1 wherein the drops of the same reagent include a same polynucleotide.

3. A method according to claim 2 wherein the same polynucleotide comprises a DNA.

4. A method according to claim 2 wherein only one cycle occurs for each of the multiple addresses.

5. A method according to claim 1 wherein:
   at least some of the deposition units are in a first line and the deposition units or the substrate, or both, is moved along a line parallel to the first line so as to form an addressable array with features in a line parallel to the first line; and
   the drops of a same reagent deposited from different deposition units during the same cycle for an address, are deposited from different deposition units along the first line.

6. A method according to claim 5 wherein the first line is straight line.

7. A method according to claim 1 additionally comprising:
   exposing the array to a sample; and
   interrogating the array following the exposure and optionally processing results of the interrogation.

8. A method according to claim 7 wherein a result of the interrogation or processing is forwarded to a remote location.

9. A method comprising transmitting data representing a result of the interrogation or processing from the method of claim 7.

10. A method of forming an addressable array of polymers on a substrate, comprising:
    (a) for each of multiple addresses on the substrate, depositing a reagent drop set during a cycle so as to attach a monomeric unit of the corresponding polymer for that address; and
    (b) repeating step (a), until the addressable array is formed;
        wherein the reagent drop set deposited during one or more cycles for one or more of the multiple addresses includes, for a corresponding cycle and address, drops of a same reagent which are deposited from different deposition units during the same cycle.

11. A method according to claim 10 wherein the polymers are biopolymers.

12. A method according to claim 10 wherein the drops of the same reagent include at least three drops of the same reagent deposited from at least three different deposition units.

13. A method according to claim 10 wherein the reagent drop set deposited for each of the addresses comprises the monomeric unit.

14. A method according to claim 13 wherein the deposition units are part of a same head so as to move as one unit, and wherein at least the head is moved with respect to the substrate.

15. A method according to claim 13 wherein:
    at least some of the deposition units are in a first line and the deposition units or the substrate, or both, is moved along a line parallel to the first line so as to form an addressable array with features in a line parallel to the first line; and the drops of a same reagent deposited from different deposition units during the same cycle for an address, are deposited from different deposition units along the first line.

16. A method of forming an addressable array of polynucleotides on a substrate, comprising:

(a) for each of multiple addresses on the substrate, depositing a reagent drop set during a cycle so as to attach a nucleoside monomer of the corresponding polymer for that address; and (b) repeating step (a), until the addressable array is formed, wherein the reagent drop set deposited during one or more cycles for one or more of the multiple addresses includes, for a corresponding cycle and address, drops of a same reagent which are deposited from different deposition units during the same cycle.

17. A method according to claim 16 wherein the drops of the same reagent include the same nucleoside monomer.

18. A method according to claim 17 wherein during each of multiple cycles for multiple addresses the reagent drop set deposited includes, for a corresponding cycle and address, drops of a same nucleoside monomer deposited from different deposition units during the cycle.

19. A method according to claim 17 wherein the drops of the same reagent include at least three drops of the same reagent deposited from at least three different deposition units.

20. A method according to claim 17 wherein:

at least some of the deposition units are in a first line and the deposition units or the substrate, or both, is moved along a line parallel to the first line so as to form an addressable array with features in a line parallel to the first line; and the drops of a same reagent deposited from different deposition units during the same cycle for an address, are deposited from different deposition units along the first line.

21. An apparatus for forming an addressable array on a substrate, comprising:

(a) a deposition system having multiple deposition units each of which can dispense a reagent drop;

(b) a transport system to move at least one of the deposition system or the substrate;

(c) a processor which controls the deposition system and the transport system such that:

i) for each of multiple addresses on the substrate, a reagent drop set is deposited by the deposition system during a cycle so as to attach a corresponding moiety for that address; and ii) step (i) will be repeated if required, until the addressable array is formed;

wherein the reagent drop set deposited during one or more cycles for one or more of the multiple addresses includes, for a corresponding cycle and address, drops of a same reagent which are deposited from different deposition units during the same cycle.

22. An apparatus according to claim 21 wherein during each of multiple cycles for multiple addresses the processor causes the reagent drop set deposited to include, for a corresponding cycle and address, a same nucleoside monomer deposited from different deposition units during the cycle.

23. An apparatus according to claim 21 wherein:

at least some of the deposition units are in a first line and at least one of the deposition system or substrate is moved by the transport system along a line parallel to the first line so as to form an addressable array with features in a line parallel to the first line; and the processor causes the drops of the same reagent to be deposited from different deposition units along the first line, during the same cycle for an address.

24. An apparatus according to claim 23 wherein the first line is a straight line.

25. A method of determining a reagent drop deposition pattern for forming an addressable array, comprising:

(a) receiving a target layout for an addressable array; and (b) determining the reagent drop deposition pattern from the target layout and the number of drop deposition units in a drop deposition system which includes multiple deposition units, which drop deposition pattern includes a definition of:

i) for each of multiple addresses on the substrate, a reagent drop set which is to be deposited during a cycle so as to attach a corresponding moiety for that address; and ii) repetitions of step (i) if required, until the addressable array is formed;

wherein the reagent drop set deposited during one or more cycles for one or more of the multiple addresses includes, for a corresponding cycle and address, drops of a same reagent which are deposited from different deposition units during the same cycle.

26. A method comprising transmitting data representing a drop deposition pattern produced by the method of claim 25.

27. A computer program product, comprising: a computer readable storage medium having a computer program stored thereon which, when loaded into a computer, performs the steps of:

(a) receiving a target layout for an addressable array; and (b) determining a reagent drop deposition pattern from the target layout and the number of drop deposition units in a drop deposition system which includes multiple deposition units, which drop deposition pattern includes a definition of:

i) for each of multiple addresses on the substrate, a reagent drop set which is to be deposited during a cycle so as to attach a corresponding moiety for that address; and ii) repetitions of step (i) if required, until the addressable array is formed;

wherein the reagent drop set deposited during one or more cycles for one or more of the multiple addresses includes, for a corresponding cycle and address, drops of a same reagent which are deposited from different deposition units during the same cycle.

28. A computer program product according to claim 27 wherein the addressable array is an array of polymers, and wherein for the drops of the same reagent include a same monomeric unit.

29. A computer program product according to claim 28 wherein the drops of the same monomeric unit include at least three drops of the same monomeric unit deposited from at least three different deposition units.

30. A computer program product according to claim 29 wherein the drop deposition pattern is additionally determined based on a configuration of the drop deposition units.

31. A computer program product according to claim 27 wherein the drops of a same reagent to be deposited from different deposition units during the same cycle for an address, are deposited from different deposition units along a first line.

32. A computer program product according to claim 31 wherein the first line is a straight line.

* * * * *